United States Patent
Rao et al.

(10) Patent No.: US 10,865,404 B1
(45) Date of Patent: Dec. 15, 2020

(54) ASPARTASE MUTANT, RECOMBINANT EXPRESSION VECTOR AND RECOMBINANT BACTERIUM CONTAINING ASPARTASE MUTANT, AND USE THEREOF

(71) Applicant: JIANGNAN UNIVERSITY, Jiangsu (CN)

(72) Inventors: Zhiming Rao, Jiangsu (CN); Yaling Wang, Jiangsu (CN); Jiamin Chen, Jiangsu (CN); Taowei Yang, Jiangsu (CN); Meijuan Xu, Jiangsu (CN); Xian Zhang, Jiangsu (CN); Minglong Shao, Jiangsu (CN); Jianing Zhang, Jiangsu (CN); Anqi Peng, Jiangsu (CN); Shuping Xu, Jiangsu (CN); Meiqi Wu, Jiangsu (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 16/901,416

(22) Filed: Jun. 15, 2020

(30) Foreign Application Priority Data

Nov. 28, 2019 (CN) .......................... 2019 1 1191601

(51) Int. Cl.
| | | |
|---|---|---|
| C12N 9/88 | (2006.01) | |
| C12N 1/21 | (2006.01) | |
| C12N 15/60 | (2006.01) | |
| C12P 13/04 | (2006.01) | |
| C12N 15/70 | (2006.01) | |

(52) U.S. Cl.
CPC .............. *C12N 9/88* (2013.01); *C12N 15/70* (2013.01); *C12P 13/04* (2013.01); *C12Y 403/01001* (2013.01)

(58) Field of Classification Search
None
See application file for complete search history.

(56) References Cited

U.S. PATENT DOCUMENTS

2020/0157522 A1* 5/2020 Wu .......................... C12N 9/88

FOREIGN PATENT DOCUMENTS

CN       108866028 A   * 11/2018

OTHER PUBLICATIONS

Uniprot, Accession No. Q9LCC6, 2017, www.uniprot.org. (Year: 2017).*
Singh et al., Current trends and developments of aspartase, Curr. Biotechnol., 2012, 1, 135-147. (Year: 2012).*
Fibriansah et al. Structural Basis for the Catalytic Mechanism of Aspartate Ammonia Lyase, Biochemistry 50, 2011, 6053-62. (Year: 2011).*
Kawata et al., Cloning and over-expression of thermostable *Bacillus* sp. YM55-1 aspartase and site-directed mutagenesis for probing a catalytic residue, Eur. J. Biochem. 267, 2000, 1847-57. (Year: 2000).*

* cited by examiner

*Primary Examiner* — Robert B Mondesi
*Assistant Examiner* — Todd M Epstein
(74) *Attorney, Agent, or Firm* — Lee & Hayes, P.C.

(57) ABSTRACT

The present invention provides an aspartase mutant, a recombinant expression vector and recombinant bacterium containing the aspartase mutant, and the use thereof, and belongs to the technical field of genetic engineering. The amino acid sequence of the aspartase mutant is as set forth in SEQ ID NO: 1. In the aspartase mutant of the present invention, on the basis of wild type aspartase (with an amino acid sequence as set out in SEQ ID NO: 3), glutamic acid at position 427 is mutated into glutamine. In the present invention, by mutating the amino acid residue at position 427 into glutamine, the polar environment near an active site is changed, and thus ammonia supply during substrate reaction is further facilitated, thereby improving an enzyme activity, enhancing the ability of the enzyme in synthesizing a β-amino acid, and providing a practical and effective strategy for industrial production of the β-amino acid.

7 Claims, 1 Drawing Sheet
Specification includes a Sequence Listing.

ID NO: 1. In the
ASPARTASE MUTANT, RECOMBINANT EXPRESSION VECTOR AND RECOMBINANT BACTERIUM CONTAINING ASPARTASE MUTANT, AND USE THEREOF

CROSS REFERENCE TO RELATED APPLICATIONS

This application claims priority to CN Patent Application No. 201911191601.4, filed Nov. 28, 2019, which is incorporated herein by reference in its entirety.

SEQUENCE LISTING INFORMATION

A computer readable textfile, entitled "B255-0005US. Sequence Listing_ST25.txt," created on or about Nov. 28, 2019 with a file size of about 16.0 KB, contains the sequence listing for this application and is hereby incorporated by reference in its entirety.

TECHNICAL FIELD

The present invention relates to the technical field of genetic engineering, and in particular to an aspartase mutant, a recombinant expression vector and recombinant bacterium containing the aspartase mutant, and the use thereof.

BACKGROUND

A β-amino acid is a target molecule that is widely used in the pharmaceutical industry, and is a structural unit of bioactive compounds or natural products and drugs. β-aminobutyric acid is an effective initiator, which can provide broad-spectrum disease protection among at least 40 plant species. Furthermore, β-aminobutyric acid can be used as a precursor of a pharmaceutical intermediate β-aminobutanol. β-aminobutanol is a key intermediate of Dolutegravir, a drug for AIDS treatment.

A natural substrate of aspartase is aspartic acid, which has been selectively modified for the preparation of the β-amino acid due to its high substrate specificity and property of secondary carboxylate binding pocket. However, the current aspartase has strict requirements on the conditions of a pH value and a temperature of the reaction, relies on a reaction environment of high temperature and strong alkali, and has a low enzyme activity under mild conditions. Such a defect leads to higher production cost of the β-amino acid.

SUMMARY

An objective of the present invention is to provide an aspartase mutant, a recombinant expression vector and recombinant bacterium containing the aspartase mutant, and the use thereof. The aspartase mutant of the present invention has an improved enzyme activity under mild conditions, can improve the reaction efficiency for preparing a β-amino acid, and meanwhile reduces the reaction cost.

In order to realize the objective of the present invention, the present invention provides the following technical solutions.

The present invention provides an aspartase mutant comprising the amino acid sequence is as set forth in SEQ ID NO: 1.

The present invention also provides a gene or nucleic acid encoding the aspartase mutant described herein, wherein the nucleotide sequence of the gene or nucleic acid is as set forth in SEQ ID NO: 2.

The present invention also provides a recombinant expression vector for the gene of the above solution.

Preferably, the recombinant expression vector comprises pET21a as an original expression vector.

The present invention also provides a recombinant bacterium including the recombinant expression vector described herein.

Preferably, the recombinant bacterium comprises *Escherichia coli* as a host bacterium.

Preferably, the *Escherichia coli* includes *E. coli* BL21.

The present invention also provides the use of the aspartase mutant or the gene or the recombinant expression vector or the recombinant bacteria of the above solution in preparation of the β-amino acid.

Preferably, the β-amino acid includes β-aminobutyric acid.

Beneficial effects of the present invention: the present invention provides an aspartase mutant, of which the amino acid sequence is as set forth in SEQ ID NO: 1. In the aspartase mutant of the present invention, the glutamic acid at position 427 of the wild type aspartase (SEQ ID NO: 3) is mutated into glutamine. In the present invention, by mutating the amino acid residue at position 427 into glutamine, the polar environment near an active site is changed, and thus ammonia supply during substrate reaction is further facilitated, thereby improving an enzyme activity, enhancing the ability of the enzyme in synthesizing a β-amino acid, and providing a practical and effective strategy for industrial production of the β-amino acid. The Test results show that, the aspartase mutant of the present invention has an increased enzyme activity compared with aspartase under different pH conditions, where the specific enzyme activity is increased by 1.36 times at a pH of 8.0; when the aspartase mutant and aspartase carry out whole-cell conversion with a substrate of crotonic acid at a pH of 9.0, the aspartase mutant of the present invention has obviously improved catalytic efficiency, where the aspartase mutant has a conversion rate of crotonic acid reaching 95% and a yield of β-aminobutyric acid reaching 228.28 g/L at 8 h. Additionally, the aspartase mutant of the present invention has an increased enzyme activity compared with aspartase at different temperatures, with the maximum increase being 1.4 times at 37° C.

DESCRIPTION OF THE EMBODIMENTS

Figure 1:
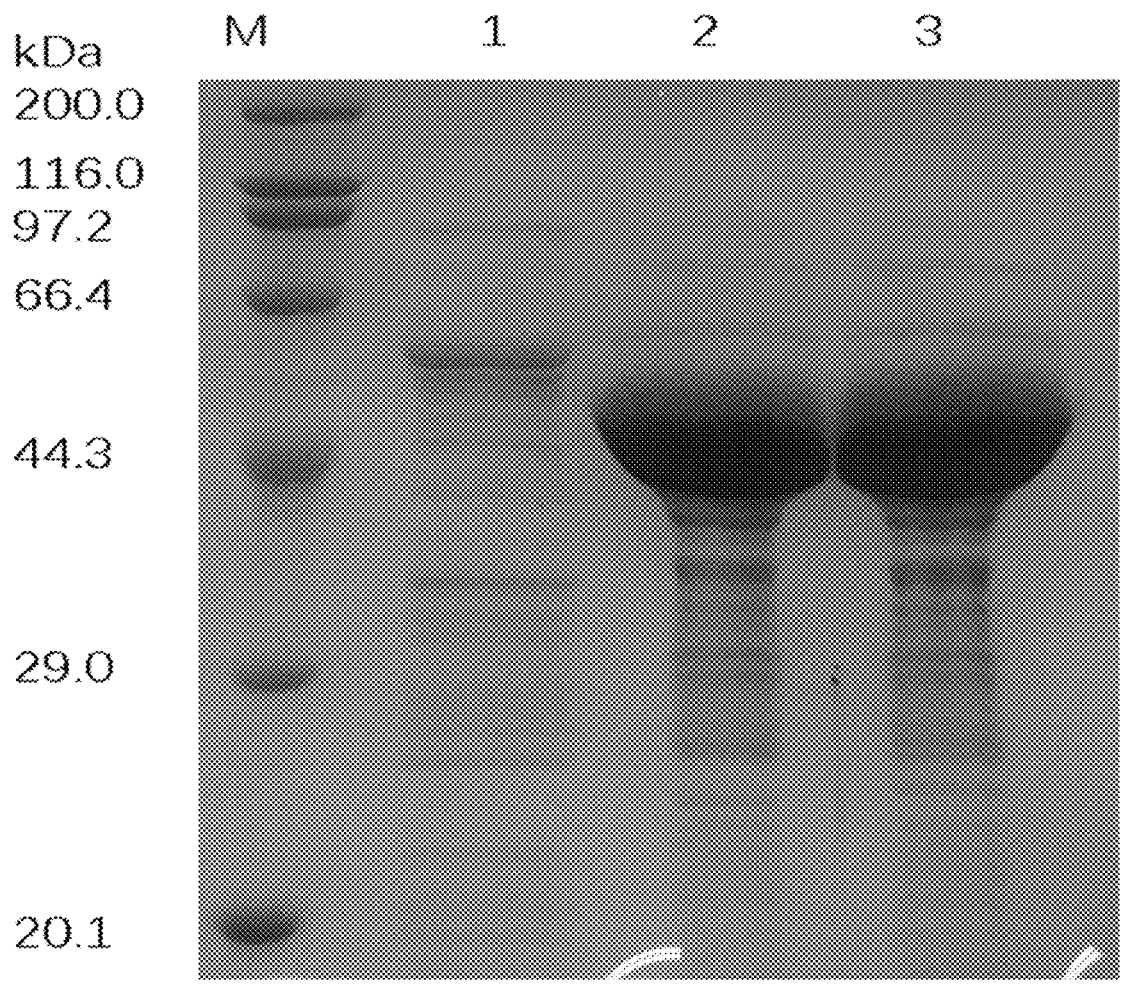
FIG. 1 is an SDS-PAGE diagram of BsAspB wild-type and mutant-type, where M represents a protein Marker; Lane 1 represents pET21a; Lane 2 represents a purified arche-type AspB; and Lane 3 represents a purified E427Q mutant.

The present invention provides an aspartase mutant (Glu427Gln) comprising the amino acid sequence is as set forth in SEQ ID NO: 1, specifically:

```
MNTDVRIEKDFLGEKEIPKDAYYGVQTIRATENFPITGYRI      50
HPELIKSLG

IVKKSAALANMEVGLLDKEVGQYIVKAADEVIEGKWNDQFI     100
VDPIQGGAG

TSINMNANEVIANRALELMGEEKGNYSKISPNSHVNMSQST     150
NDAFPTATH

IAVLSLLNQLIETTKYMQQEFMKKADEFAGVIKMGRCHLQD     200
AVPILLGQE
```

```
FEAYARVIARDIERIANTRNNLYDINMGATAVGTGLNADPE      250
YISIVTEHL

AKFSGHPLRSAQHLVDATQNTDCYTEVSSALKVCMINMSKI      300
ANDLRLMAS

GPRAGLSEIVLPARQPGSSTIPGLVAPVMPEVMNQVAFQVF      350
GNDLTITSA

SEAGQFELNVMEPVLFFNLIQSISIMTNVFKSFTENCLKGI      400
KANEERMKE

YVEKSIGIITAINPHVGYETAAKLARQAYLTGESIRELCIK      450
YGVLTEEQLNEILNPYEMTHPGIAGRK*.
```

The amino acid sequence of the wild type aspartase is as set forth in SEQ ID NO: 3, specifically:

```
MNTDVRIEKDFLGEKEIPKDAYYGVQTIRATENFPITGYRI       50
HPELIKSLG

IVKKSAALANMEVGLLDKEVGQYIVKAADEVIEGKWNDQFI      100
VDPIQGGAG

TSINMNANEVIANRALELMGEEKGNYSKISPNSHVNMSQST      150
NDAFPTATH

IAVLSLLNQLIETTKYMQQEFMKKADEFAGVIKMGRCHLQD      200
AVPILLGQE

FEAYARVIARDIERIANTRNNLYDINMGATAVGTGLNADPE      250
YISIVTEHL

AKFSGHPLRSAQHLVDATQNTDCYTEVSSALKVCMINMSKI      300
ANDLRLMAS

GPRAGLSEIVLPARQPGSSIIPGLVAPVMPEVMNQVAFQVF      350
GNDLTITSA

SEAGQFELNVMEPVLFFNLIQSISIMTNVFKSFTENCLKGI      400
KANEERMKE

YVEKSIGIITAINPHVGYETAAKLAREAYLTGESIRELCIK      450
YGVLTEEQLNEILNPYEMTHPGIAGRK*).
```

The glutamic acid at position 427 of the wild type aspartase is mutated into glutamine to obtain the aspartase mutant of the present invention. In the present invention, by mutating the amino acid residue at position 427 into glutamine, the polar environment near an active site is changed, and thus ammonia supply during substrate reaction is further facilitated, thereby improving an enzyme activity, and enhancing the ability of the enzyme in synthesizing a β-amino acid.

The present invention also provides a gene (E427Q) encoding the aspartase mutant of the aforementioned technical solution, where the nucleotide sequence of the gene is as set forth in SEQ ID NO: 2, specifically:

```
ATGAACACCGATGTGCGCATCGAGAAAGACTTTCTGGGCGAGAAGGAAA

TCCCGAAAGACGCGTACTACGGCGTGCAGACCATCCGCGCCACGGAAAA

CTTCCCGATTACCGGCTACCGCATTCACCCAGAGCTGATTAAGAGCCTC

GGCATCGTGAAAAAGAGCGCCGCGCTGGCCAACATGGAAGTTGGTCTGC

TGGACAAAGAGGTTGGCCAGTACATCGTGAAAGCCGCCGACGAAGTGAT

CGAGGGTAAGTGGAACGACCAGTTCATCGTGGACCCAATCCAAGGCGGT

GCGGGCACCAGCATCAACATGAACGCGAACGAGGTGATCGCGAATCGTG

CGCTGGAACTGATGGGCGAGGAAAAGGGCAACTACAGCAAGATTAGCCC

AAACAGCCACGTGAATATGAGCCAGAGCACCAACGATGCGTTCCCAACG

GCCACCCACATCGCCGTTCTGAGTCTGCTGAATCAGCTCATCGAGACGA

CCAAGTATATGCAGCAAGAGTTCATGAAGAAAGCGGATGAGTTTGCGGG

CGTGATCAAGATGGGTCGCTGTCATCTGCAAGATGCGGTGCCGATTCTG

CTGGGCCAAGAGTTCGAAGCCTACGCGCGCGTTATCGCGCGCGACATTG

AACGCATCGCCAACACCCGCAACAATCTCTACGACATCAACATGGGCGC

GACCGCCGTTGGTACGGGTCTCAACGCCGACCCAGAGTACATCAGCATC

GTGACCGAACATCTGGCCAAATTCAGTGGTCACCCGCTCCGTAGCGCGC

AGCATCTCGTGGATGCGACGCAGAATACCGATTGCTACACGGAGGTGAG

CAGCGCGCTCAAAGTGTGCATGATCAACATGAGCAAAATCGCCAACGAT

CTCCGTCTGATGGCCAGTGGTCCACGTGCCGGTCTGAGTGAAATTGTTC

TGCCGGCGCGTCAACCGGGCAGCAGTATTATCCCGGGTCTGGTTGCGCC

AGTTATGCCGGAGGTTATGAATCAAGTTGCCTTCCAAGTTTTCGGTAAC

GATCTGACGATCACGAGCGCCAGCGAAGCGGGCCAGTTTGAGCTCAACG

TTATGGAGCCGGTTCTGTTCTTCAACCTCATCCAGAGCATTAGCATCAT

GACGAATGTGTTCAAAAGCTTTACGGAAAACTGCCTCAAAGGCATCAAG

GCCAACGAGGAGCGTATGAAGGAGTACGTGGAAAAGAGCATCGGCATCA

TCACCGCGATCAATCCGCATGTGGGCTATGAAACCGCGGCGAAGCTGGC

CCGTCAAGCGTACCTCACCGGTGAAAGCATCCGCGAGCTGTGCATCAAG

TACGGCGTTCTCACCGAGGAGCAGCTGAACGAGATTCTGAACCCGTATG

AGATGACGCACCCGGGTATCGCCGGTCGTAAGTAA.
```

The gene E427Q of the present invention is a mutation of a codon encoding glutamic acid at position 427 of the wild type aspartase into a codon encoding glutamine. The nucleotide sequence of the gene encoding the wild type aspartase is as set forth in SEQ ID NO: 4, specifically:

```
ATGAACACCGATGTGCGCATCGAGAAAGACTTTCTGGGCGAGAAGGAAA

TCCCGAAAGACGCGTACTACGGCGTGCAGACCATCCGCGCCACGGAAAA

CTTCCCGATTACCGGCTACCGCATTCACCCAGAGCTGATTAAGAGCCTC

GGCATCGTGAAAAAGAGCGCCGCGCTGGCCAACATGGAAGTTGGTCTGC

TGGACAAAGAGGTTGGCCAGTACATCGTGAAAGCCGCCGACGAAGTGAT

CGAGGGTAAGTGGAACGACCAGTTCATCGTGGACCCAATCCAAGGCGGT

GCGGGCACCAGCATCAACATGAACGCGAACGAGGTGATCGCGAATCGTG

CGCTGGAACTGATGGGCGAGGAAAAGGGCAACTACAGCAAGATTAGCCC

AAACAGCCACGTGAATATGAGCCAGAGCACCAACGATGCGTTCCCAACG

GCCACCCACATCGCCGTTCTGAGTCTGCTGAATCAGCTCATCGAGACGA

CCAAGTATATGCAGCAAGAGTTCATGAAGAAAGCGGATGAGTTTGCGGG

CGTGATCAAGATGGGTCGCTGTCATCTGCAAGATGCGGTGCCGATTCTG

CTGGGCCAAGAGTTCGAAGCCTACGCGCGCGTTATCGCGCGCGACATTG

AACGCATCGCCAACACCCGCAACAATCTCTACGACATCAACATGGGCGC

GACCGCCGTTGGTACGGGTCTCAACGCCGACCCAGAGTACATCAGCATC
```

-continued
```
GTGACCGAACATCTGGCCAAATTCAGTGGTCACCCGCTCCGTAGCGCGC

AGCATCTCGTGGATGCGACGCAGAATACCGATTGCTACACGGAGGTGAG

CAGCGCGCTCAAAGTGTGCATGATCAACATGAGCAAAATCGCCAACGAT

CTCCGTCTGATGGCCAGTGGTCCACGTGCCGGTCTGAGTGAAATTGTTC

TGCCGGCGCGTCAACCGGGCAGCAGTATTATCCCGGGTCTGGTTGCGCC

AGTTATGCCGGAGGTTATGAATCAAGTTGCCTTCCAAGTTTTCGGTAAC

GATCTGACGATCACGAGCGCCAGCGAAGCGGGCCAGTTTGAGCTCAACG

TTATGGAGCCGGTTCTGTTCTTCAACCTCATCCAGAGCATTAGCATCAT

GACGAATGTGTTCAAAAGCTTTACGGAAAACTGCCTCAAAGGCATCAAG

GCCAACGAGGAGCGTATGAAGGAGTACGTGGAAAAGAGCATCGGCATCA

TCACCGCGATCAATCCGCATGTGGGCTATGAAACCGCGGCGAAGCTGGC

CCGTGAAGCGTACCTCACCGGTGAAAGCATCCGCGAGCTGTGCATCAAG

TACGGCGTTCTCACCGAGGAGCAGCTGAACGAGATTCTGAACCCGTATG

AGATGACGCACCCGGGTATCGCCGGTCGTAAGTAA.
```

The present invention also provides a recombinant expression vector for the gene E427Q of the above solution; the recombinant expression vector preferably uses pET21a as an original expression vector; the gene E427Q is preferably inserted between EcoRI and BamHI on the plasmid pET21a; the present invention has no specific limitation of the method for constructing the recombinant vector, and a conventional method in the art can be adopted. During the implementation of the present invention, the recombinant vector is constructed by the following method: performing PCR by using the nucleotide sequence as set forth in SEQ ID NO:4 as a template and using Flprimer (with the sequence as set forth in SEQ ID NO: 5, specifically:

GCGAAGCTGGCCCGTCAGGCGTACCTCACCGGT and Rlprimer (with the sequence as set forth in SEQ ID NO: 6, specifically:

GCCTTACTGGTTAGCAGAATG as primers to obtain a gene E427Q as set forth in SEQ ID NO: 3; ligating the gene E427Q into the pET21a expression vector to obtain a recombinant expression vector pET21a-E427Q.

The present invention also provides a recombinant bacterium comprising the recombinant expression vector of the above solution; the recombinant bacterium preferably uses *Escherichia coli* as a host bacterium; the *Escherichia coli* preferably includes *E. coli* BL21 (DE3); and the present invention has no specific limitation on the method for constructing the recombinant bacterium, and a conventional method in the art can be adopted. During the implementation of the present invention, the recombinant bacterium is prepared by the following method: transforming the recombinant expression vector pET21a-E427Q into *E. coli* BL21 to obtain a recombinant bacterium named pET21a-E427Q/ *E. coli* BL21.

The aspartase mutant in the present invention is preferably prepared by the following method: culturing the recombinant bacterium, and inducing to obtain a aspartase mutant; where the culture medium for culturing the recombinant bacterium is preferably a LB culture medium; the LB culture medium contains 10 g/L of peptone, 5 g/L of a yeast extract and 10 g/L of sodium chloride; the pH value of the LB culture medium is 7.2; the culture temperature is preferably 37° C.; the culture time is defined when the OD600 of the culture reaches 0.6-0.9; and the induction manner is preferably adding isopropyl-β-D-thiogalactopyranoside (IPTG) with a final concentration of 0.1-1.0 mM into the culture medium, to conduct induction culture at 16° C. for 12-16 h.

The present invention also provides the use of the aspartase mutant or the gene or the recombinant expression vector or the recombinant bacterium of the above solution in the preparation of a β-amino acid; and the β-amino acid preferably includes β-aminobutyric acid.

During the implementation of the present invention, without any coenzyme, by using crotonic acid as a substrate, the aspartase mutant or the recombinant bacterium thereof reacts in a conversion reaction system composed of a buffer solution with a pH value of 7.0-9.5 at 37-55° C. for 2-12 h to obtain a formulation including the aspartase mutant; the initial concentration of the substrate in the conversion system is preferably 300 mM; the concentration of the aspartase mutant in the conversion system is preferably 0.1-3 mg protein/mL reaction solution; the mass of the recombinant bacterium in the conversion system is preferably 1-400 g/L by the wet weight of the bacterium; the reagent for adjusting the pH value is preferably ammonium hydroxide with a percentage mass content of 25%; and the pH value of the conversion reaction system is preferably 8-9.

In the present invention, after obtaining the formulation including the aspartase mutant, it preferably further includes separating and purifying the aspartase mutant from the formulation, preferably by the following method: heating to remove precipitated proteins or thallus, centrifuging the reaction solution, taking the supernatant and removing pigments from it through activated carbon adsorption, subjecting to reduced pressure distillation, and then saturated crystallization or ethanol precipitation crystallization to obtain a crude product.

In the present invention, after obtaining the crude product, it preferably further includes purifying the crude product. The present invention has no specific limitation on the method of purifying the crude product, and a conventional purification method in the art can be adopted. The purification method adopted during the implementation of the present invention includes chromatographic separation or adsorption separation.

The technical solution provided by the present invention will be described in detail in connection with the following examples, but they should not be construed as limiting the claimed scope of the present invention.

Definition of enzyme activity: the amount of enzyme required to convert 1 μmol of crotonic acid into β-aminobutyric acid per minute is defined as one enzyme activity unit U. The unit of enzyme activity is U/mL. The specific enzyme activity is defined as the enzyme activity of a unit protein, in U/mg.

Enzyme Activity Determination of aspartase: a reaction system (200 μL) composed of 300 mM ammonia, 100 mM Na2HPO4 and 300 mM crotonic acid, with the pH being adjusted to 7-9.5 with 5 M NaOH, is added with an appropriate amount of enzyme solution to start a reaction that react at 37-55° C. for 3 h, and the enzyme activity is calculated according to the yield of β-aminobutyric acid in the reaction.

Example 1 Construction of a Recombinant Expression Vector Containing a Gene Encoding a Aspartase Mutant A mutant plasmid (the reaction system was as shown in Table 1 and the reaction conditions were as shown in Table 2) is constructed using a whole-plasmid two-step PCR method by using a pET-21a recombinant plasmid containing the nucleotide sequence as set in SEQ ID NO: 4 as a template and using Fprimer (with the sequence as set out in SEQ ID NO: 5) and Rprimer (with the sequence as set forth in SEQ ID NO: 6) as primers, so as to obtain a gene E427Q as set forth in SEQ ID NO: 3.

TABLE 1

PCR Reaction System

| Reaction System | Volume |
| --- | --- |
| Primer F | 0.2 L |
| Primer R | 0.2 L |
| Template plasmid | 0.25 L |
| 5X PCR Buffer | 5 L |
| dNTPs (2.5 mM) | |
| PrimerSTAR HS DNA polymerase | 2 L |
| | 0.25 L |
| ddH$_2$O | 17.1 L |
| Total volume | 25 L |

TABLE 2

PCR Reaction Conditions

| Steps for PCR | Conditions for PCR | |
| --- | --- | --- |
| Pre-denaturating | 95° C., 3 min | (denaturating, annealing) cycling for 5 batches |
| Denaturating | 95° C., 30 s | |
| Annealing | 55° C., 1 min | |
| Extending | 72° C., 1 min × large-fragment primer kb | |
| Denaturation | | |
| Extending | 95° C., 30 s | (denaturating, extending) cycling for 25 batches |
| Fully extending | 68° C., 1 min × template kb | |
| low-temperature preservation | 68° C., 2 min × template kb | |
| | 4° C., forever | |

The PCR product was examined by gel electrophoresis, then 20 µL of the PCR product was added with 1 µL of Dpn I restriction endonuclease to digest the template plasmid, and incubated at 25° C. overnight or at 37° C. for 3-4 h. 5 µL of the enzyme-digested product was pipetted and transformed into *E. coli* BL21 (DE3) to obtain a corresponding recombinant *E. coli*. The recombinant *E. coli* was spread onto a LB plate containing ampicillin (100 mg/L), cultured overnight at 37° C., and then clones were randomly picked for colony PCR identification and sequencing verification. The results showed that the recombinant expression vector containing the gene encoding the aspartase mutant had been successfully transformed into the expression host *E. coli* BL21 (DE3), and was named pET21a-E427Q. The bacterial solution in which the mutant is successful as verified by sequencing, was added with glycerol, and stored in a refrigerator at −70° C. The sequencing work was completed by GENEWIZ in Suzhou.

Example 2 Construction of a Recombinant *Escherichia coli* Engineering Strain Producing the Aspartase Mutant The strain containing the correct recombinant plasmid pET21a-E427Q as obtained in Example 1 was the recombinant strain pET21a-E427Q/*E. coli* BL21 of the present invention.

Example 3 Expression of Aspartase by the Recombinant Strain pET21a-E427Q/*E. coli* BL21, and Purification of the Same The recombinant strain pET21a-E427Q/*E. coli* BL21 as constructed in Example 2 and a control strain pET21a-AspB/*E. coli* BL21 expressing the unmutated original enzyme BsAspB (wild-type, with the amino acid sequence as set out in SEQ ID NO: 3) were respectively inoculated in 10 mL of a LB medium containing ampicillin and cultured overnight at 37° C. under shaking. The next day, they were each transferred to 50 mL of a LB medium containing ampicillin at the inoculation size of 1%, cultured at 37° C. for 2-3 h, and then added with 0.5 mM IPTG to induce at 16° C. for 12-16 h. They were each centrifuged at 8000 rpm and 4° C. for 10 min, and then cells were collected and crushed, and the supernatant of cell crushing (crude enzyme solution) was collected for subsequent purification.

The purification of aspartase or the aspartase mutant is conducted by placing in a hot water bath at 60° C. for 30 min, and then centrifuging at 12,000 rmp for 90 min to obtain a purified enzyme. The purified enzyme was stored at 4° C. for later use. The purified enzyme solution was analyzed by SDS-PAGE. The results were as shown in FIG. 1, where M represented a protein Marker; Lane 1 represented pET21a; Lane 2 represented a purified arche-type AspB; and Lane 3 represented a purified E427Q mutant. The results showed that electrophoretically pure recombinant aspartase and the mutant thereof were obtained.

Example 4 Enzyme Activity Determination of Aspartase and HPLC Detection of β-Aminobutyric Acid The original enzyme and the mutant enzyme were tested for enzyme activities under different conditions of 37° C., 45° C., and 55° C. (pH 8.0) and pH 7.0, 8.0, 9.0, 9.5 (37° C.). After 3 h of reaction, the content of β-aminobutyric acid was determined by HPLC.

HPLC: 100 µL of the reaction solution was taken, added with 40 µL of 1M NaHCO$_3$, mixed well, then added with 160 µL of 2,4-dinitrofluorobenzene (20.48 mg dissolved in 3 mL of acetone) to react for 1 h in the dark at 60° C., then taken out and centrifuged, and filtered through a 0.22 µm membrane. Then sample loading was conducted. Chromatographic column: dimosoil C18 (5 µL, 250 mm×4.6 mm), the mobile phase: A: aqueous solution of 0.1% formic acid, B: 100% acetonitrile, the detector: an UV Detector, the detection wavelength: 360 nm, the column temperature: 25° C., the sample size: 10 µL, and the flow rate: 1.0 mL/min. Process: 0-22 min: 15% B→50% B; 22-22.1 min:50% B→15% B; 22.1-26 min:15% B.

The calculated specific enzyme activities of the original enzyme and the mutant enzyme E427Q were as shown in Tables 3 and 4. The results showed that, the specific enzyme activity of the E427Q mutant was 1.36 times higher than that of the original enzyme at pH 8.0, but the optimal reaction pH of both of them was 9.0, and thus they were dependent on alkaline conditions. Under different temperatures, the specific enzyme activities of both of them were increased gradually along with the increase of temperature, but at 37° C., the specific enzyme activity was increased most significantly, by about 1.4 times. This was related to the change of the polar environment near the active site after mutation of the site 427, which was more conducive to the supply of ammonia, and thus promoted the enzymatic reaction.

TABLE 3

Specific enzyme activities (mU/mg) of the original enzyme and E427Q at different pHs (37° C.)

| Enzyme | pH 7.0 | pH 8.0 | pH 9.0 | pH 9.5 |
|---|---|---|---|---|
| AspB | 0.1626 | 0.5902 | 1.5153 | 1.2863 |
| E427Q | 0.1903 | 0.8044 | 1.8606 | 1.3903 |

TABLE 4

Specific enzyme activities (mU/mg) of the original enzyme and E427Q at different temperatures (pH 8.0)

| Enzyme | 37° C. | 45° C. | 55° C. |
|---|---|---|---|
| AspB | 0.5902 | 0.8610 | 1.1738 |
| E427Q | 0.8044 | 0.9570 | 1.2416 |

Example 5 Preparation of β-Aminobutyric Acid by Arche-Type Aspartase and its Mutant E427Q Engineering Strain The AspB arche-type and E427Q mutant-type engineering strains in Example 2 were used for conversion of the substrate of crotonic acid. A 10 mL conversion system containing 200 g/L of the substrate of crotonic acid in a buffer solution consisting of Tris-HCl containing 2 mM of MgCl2, with the pH being adjusted to 9.0 by adding 25% ammonium hydroxide and the bacterial count OD=44, reacted at 55° C. for 8 h. The yield of β-aminobutyric acid was as shown in table 5. The results showed that, the catalytic efficiency of the mutant enzyme was significantly improved. After 4 h of reaction, the yield of the mutant enzyme E427Q engineering strain was 1.3 times that of the arche-type whole-cell conversion. After 8 h of reaction, the conversion rate of the substrate by the mutant enzyme had reached 95%. Meanwhile, both the original enzyme and the mutant E427Q showed good stereoselectivity, and the enantiomeric excess value of the product remained above 99%. This indicated that the aspartase mutant has broad industrial application prospects.

TABLE 5

Yields (g/L) of β-aminobutyric acid by the arche-type Enzyme and E427Q whole-cell conversion

| Enzyme | 2 h | 4 h | 6 h | 8 h |
|---|---|---|---|---|
| AspB | 32.31 | 129.69 | 209.59 | 209.32 |
| E427Q | 64.11 | 167.72 | 222.29 | 228.28 |

The above description is only preferred embodiments of the present invention. It should be pointed out that, for those of ordinary skills in the art, several improvements and modifications can be made without departing from the principle of the present invention. These improvements and modifications should also be considered as falling into the claimed scope of the present invention.

What is claimed is:

1. An aspartase mutant, wherein the aspartase mutant comprises amino acid sequence as set forth in SEQ ID NO: 1.

2. A recombinant expression vector comprising a nucleic acid encoding the aspartase mutant according to claim 1.

3. The recombinant expression vector according to claim 2, wherein the nucleic acid comprises nucleic acid sequence as set forth in SEQ ID NO: 2.

4. The recombinant expression vector according to claim 2, wherein the recombinant expression vector comprises pET21a.

5. A recombinant bacterium comprising the recombinant expression vector according to claim 2.

6. The recombinant bacterium according to claim 5, wherein the recombinant bacterium comprises *Escherichia coli*.

7. The recombinant bacterium according to claim 6, wherein the *Escherichia coli* comprises *E. coli* BL21.

\* \* \* \* \*

UNITED STATES PATENT AND TRADEMARK OFFICE
CERTIFICATE OF CORRECTION

| | | |
|---|---|---|
| PATENT NO. | : 10,865,404 B1 | Page 1 of 1 |
| APPLICATION NO. | : 16/901416 | |
| DATED | : December 15, 2020 | |
| INVENTOR(S) | : Zhiming Rao et al. | |

It is certified that error appears in the above-identified patent and that said Letters Patent is hereby corrected as shown below:

On the Title Page

Item (30) Foreign Application Priority Data, change "Nov. 28, 2019 (CN) .......... 201911191601" to -- Nov. 28, 2019 (CN) .......... 201911191601.4 --

Signed and Sealed this
Third Day of August, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 6

<210> SEQ ID NO 1
<211> LENGTH: 468
<212> TYPE: PRT
<213> ORGANISM: artificial sequence
<220> FEATURE:
<223> OTHER INFORMATION: the amino acid sequence of an aspartase mutant

<400> SEQUENCE: 1

Met Asn Thr Asp Val Arg Ile Glu Lys Asp Phe Leu Gly Glu Lys Glu
1               5                   10                  15

Ile Pro Lys Asp Ala Tyr Tyr Gly Val Gln Thr Ile Arg Ala Thr Glu
            20                  25                  30

Asn Phe Pro Ile Thr Gly Tyr Arg Ile His Pro Glu Leu Ile Lys Ser
        35                  40                  45

Leu Gly Ile Val Lys Lys Ser Ala Ala Leu Ala Asn Met Glu Val Gly
    50                  55                  60

Leu Leu Asp Lys Glu Val Gly Gln Tyr Ile Val Lys Ala Ala Asp Glu
65                  70                  75                  80

Val Ile Glu Gly Lys Trp Asn Asp Gln Phe Ile Val Asp Pro Ile Gln
                85                  90                  95

Gly Gly Ala Gly Thr Ser Ile Asn Met Asn Ala Asn Glu Val Ile Ala
            100                 105                 110

Asn Arg Ala Leu Glu Leu Met Gly Glu Glu Lys Gly Asn Tyr Ser Lys
        115                 120                 125
```

```
Ile Ser Pro Asn Ser His Val Asn Met Ser Gln Ser Thr Asn Asp Ala
    130                 135                 140

Phe Pro Thr Ala Thr His Ile Ala Val Leu Ser Leu Leu Asn Gln Leu
145                 150                 155                 160

Ile Glu Thr Thr Lys Tyr Met Gln Gln Glu Phe Met Lys Lys Ala Asp
                165                 170                 175

Glu Phe Ala Gly Val Ile Lys Met Gly Arg Cys His Leu Gln Asp Ala
            180                 185                 190

Val Pro Ile Leu Leu Gly Gln Glu Phe Glu Ala Tyr Ala Arg Val Ile
        195                 200                 205

Ala Arg Asp Ile Glu Arg Ile Ala Asn Thr Arg Asn Asn Leu Tyr Asp
    210                 215                 220

Ile Asn Met Gly Ala Thr Ala Val Gly Thr Gly Leu Asn Ala Asp Pro
225                 230                 235                 240

Glu Tyr Ile Ser Ile Val Thr Glu His Leu Ala Lys Phe Ser Gly His
                245                 250                 255

Pro Leu Arg Ser Ala Gln His Leu Val Asp Ala Thr Gln Asn Thr Asp
            260                 265                 270

Cys Tyr Thr Glu Val Ser Ser Ala Leu Lys Val Cys Met Ile Asn Met
        275                 280                 285

Ser Lys Ile Ala Asn Asp Leu Arg Leu Met Ala Ser Gly Pro Arg Ala
    290                 295                 300

Gly Leu Ser Glu Ile Val Leu Pro Ala Arg Gln Pro Gly Ser Ser Ile
305                 310                 315                 320

Ile Pro Gly Leu Val Ala Pro Val Met Pro Glu Val Met Asn Gln Val
                325                 330                 335

Ala Phe Gln Val Phe Gly Asn Asp Leu Thr Ile Thr Ser Ala Ser Glu
            340                 345                 350

Ala Gly Gln Phe Glu Leu Asn Val Met Glu Pro Val Leu Phe Phe Asn
        355                 360                 365

Leu Ile Gln Ser Ile Ser Ile Met Thr Asn Val Phe Lys Ser Phe Thr
    370                 375                 380

Glu Asn Cys Leu Lys Gly Ile Lys Ala Asn Glu Arg Met Lys Glu
385                 390                 395                 400

Tyr Val Glu Lys Ser Ile Gly Ile Ile Thr Ala Ile Asn Pro His Val
                405                 410                 415

Gly Tyr Glu Thr Ala Ala Lys Leu Ala Arg Gln Ala Tyr Leu Thr Gly
            420                 425                 430

Glu Ser Ile Arg Glu Leu Cys Ile Lys Tyr Gly Val Leu Thr Glu Glu
        435                 440                 445

Gln Leu Asn Glu Ile Leu Asn Pro Tyr Glu Met Thr His Pro Gly Ile
    450                 455                 460

Ala Gly Arg Lys
465

<210> SEQ ID NO 2
<211> LENGTH: 1407
<212> TYPE: DNA
<213> ORGANISM: artificial sequence
<220> FEATURE:
<223> OTHER INFORMATION: the nucleotide sequence of the gene encoding
      the aspartase mutant

<400> SEQUENCE: 2
atgaacaccg atgtgcgcat cgagaaagac tttctgggcg agaaggaaat cccgaaagac      60
```
gcgtactacg gcgtgcagac catccgcgcc acggaaaact tcccgattac cggctaccgc    120
attcacccag agctgattaa gagcctcggc atcgtgaaaa agagcgccgc gctggccaac    180
atggaagttg gtctgctgga caaagaggtt ggccagtaca tcgtgaaagc cgccgacgaa    240
gtgatcgagg gtaagtggaa cgaccagttc atcgtggacc caatccaagg cggtgcgggc    300
accagcatca acatgaacgc gaacgaggtg atcgcgaatc gtgcgctgga actgatgggc    360
gaggaaaagg gcaactacag caagattagc ccaaacagcc acgtgaatat gagccagagc    420
accaacgatg cgttcccaac ggccacccac atcgccgttc tgagtctgct gaatcagctc    480
atcgagacga ccaagtatat gcagcaagag ttcatgaaga aagcggatga gtttgcgggc    540
gtgatcaaga tgggtcgctg tcatctgcaa gatgcggtgc cgattctgct gggccaagag    600
ttcgaagcct acgcgcgcgt tatcgcgcgc gacattgaac gcatcgccaa cacccgcaac    660
aatctctacg acatcaacat gggcgcgacc gccgttggta cgggtctcaa cgccgaccca    720
gagtacatca gcatcgtgac cgaacatctg gccaaattca gtggtcaccc gctccgtagc    780
gcgcagcatc tcgtggatgc gacgcagaat accgattgct acacggaggt gagcagcgcg    840
ctcaaagtgt gcatgatcaa catgagcaaa atcgccaacg atctccgtct gatggccagt    900
ggtccacgtg ccggtctgag tgaaattgtt ctgccggcgc gtcaaccggg cagcagtatt    960
atcccgggtc tggttgcgcc agttatgccg gaggttatga atcaagttgc cttccaagtt   1020
ttcggtaacg atctgacgat cacgagcgcc agcgaagcgg gccagtttga gctcaacgtt   1080
atggagccgg ttctgttctt caacctcatc cagagcatta gcatcatgac gaatgtgttc   1140
aaaagcttta cggaaaactg cctcaaaggc atcaaggcca acgaggagcg tatgaaggag   1200
tacgtggaaa agagcatcgg catcatcacc gcgatcaatc cgcatgtggg ctatgaaacc   1260
gcggcgaagc tggcccgtca agcgtacctc accggtgaaa gcatccgcga gctgtgcatc   1320
aagtacggcg ttctcaccga ggagcagctg aacgagattc tgaacccgta tgagatgacg   1380
cacccgggta tcgccggtcg taagtaa                                       1407

<210> SEQ ID NO 3
<211> LENGTH: 468
<212> TYPE: PRT
<213> ORGANISM: artificial sequence
<220> FEATURE:
<223> OTHER INFORMATION: an amino acid sequence of aspartase

<400> SEQUENCE: 3

Met Asn Thr Asp Val Arg Ile Glu Lys Asp Phe Leu Gly Glu Lys Glu
1               5                   10                  15

Ile Pro Lys Asp Ala Tyr Tyr Gly Val Gln Thr Ile Arg Ala Thr Glu
            20                  25                  30

Asn Phe Pro Ile Thr Gly Tyr Arg Ile His Pro Glu Leu Ile Lys Ser
        35                  40                  45

Leu Gly Ile Val Lys Lys Ser Ala Ala Leu Ala Asn Met Glu Val Gly
    50                  55                  60

Leu Leu Asp Lys Glu Val Gly Gln Tyr Ile Val Lys Ala Ala Asp Glu
65                  70                  75                  80

Val Ile Glu Gly Lys Trp Asn Asp Gln Phe Ile Val Asp Pro Ile Gln
                85                  90                  95

Gly Gly Ala Gly Thr Ser Ile Asn Met Asn Ala Asn Glu Val Ile Ala
            100                 105                 110

Asn Arg Ala Leu Glu Leu Met Gly Glu Glu Lys Gly Asn Tyr Ser Lys

```
            115                 120                 125
Ile Ser Pro Asn Ser His Val Asn Met Ser Gln Ser Thr Asn Asp Ala
130                 135                 140

Phe Pro Thr Ala Thr His Ile Ala Val Leu Ser Leu Leu Asn Gln Leu
145                 150                 155                 160

Ile Glu Thr Thr Lys Tyr Met Gln Gln Glu Phe Met Lys Lys Ala Asp
                165                 170                 175

Glu Phe Ala Gly Val Ile Lys Met Gly Arg Cys His Leu Gln Asp Ala
                180                 185                 190

Val Pro Ile Leu Leu Gly Gln Glu Phe Glu Ala Tyr Ala Arg Val Ile
                195                 200                 205

Ala Arg Asp Ile Glu Arg Ile Ala Asn Thr Arg Asn Asn Leu Tyr Asp
        210                 215                 220

Ile Asn Met Gly Ala Thr Ala Val Gly Thr Gly Leu Asn Ala Asp Pro
225                 230                 235                 240

Glu Tyr Ile Ser Ile Val Thr Glu His Leu Ala Lys Phe Ser Gly His
                245                 250                 255

Pro Leu Arg Ser Ala Gln His Leu Val Asp Ala Thr Gln Asn Thr Asp
            260                 265                 270

Cys Tyr Thr Glu Val Ser Ser Ala Leu Lys Val Cys Met Ile Asn Met
            275                 280                 285

Ser Lys Ile Ala Asn Asp Leu Arg Leu Met Ala Ser Gly Pro Arg Ala
            290                 295                 300

Gly Leu Ser Glu Ile Val Leu Pro Ala Arg Gln Pro Gly Ser Ser Ile
305                 310                 315                 320

Ile Pro Gly Leu Val Ala Pro Val Met Pro Glu Val Met Asn Gln Val
                325                 330                 335

Ala Phe Gln Val Phe Gly Asn Asp Leu Thr Ile Thr Ser Ala Ser Glu
                340                 345                 350

Ala Gly Gln Phe Glu Leu Asn Val Met Glu Pro Val Leu Phe Phe Asn
            355                 360                 365

Leu Ile Gln Ser Ile Ser Ile Met Thr Asn Val Phe Lys Ser Phe Thr
370                 375                 380

Glu Asn Cys Leu Lys Gly Ile Lys Ala Asn Glu Arg Met Lys Glu
385                 390                 395                 400

Tyr Val Glu Lys Ser Ile Gly Ile Ile Thr Ala Ile Asn Pro His Val
                405                 410                 415

Gly Tyr Glu Thr Ala Ala Lys Leu Ala Arg Glu Ala Tyr Leu Thr Gly
                420                 425                 430

Glu Ser Ile Arg Glu Leu Cys Ile Lys Tyr Gly Val Leu Thr Glu Glu
            435                 440                 445

Gln Leu Asn Glu Ile Leu Asn Pro Tyr Glu Met Thr His Pro Gly Ile
        450                 455                 460

Ala Gly Arg Lys
465

<210> SEQ ID NO 4
<211> LENGTH: 1407
<212> TYPE: DNA
<213> ORGANISM: artificial sequence
<220> FEATURE:
<223> OTHER INFORMATION: the nucleotide sequence of the gene encoding
      aspartase

<400> SEQUENCE: 4
```

-continued

| | |
|---|---|
| atgaacaccg atgtgcgcat cgagaaagac tttctgggcg agaaggaaat cccgaaagac | 60 |
| gcgtactacg gcgtgcagac catccgcgcc acggaaaact tcccgattac cggctaccgc | 120 |
| attcacccag agctgattaa gagcctcggc atcgtgaaaa agagcgccgc gctggccaac | 180 |
| atggaagttg gtctgctgga caaagaggtt ggccagtaca tcgtgaaagc cgccgacgaa | 240 |
| gtgatcgagg gtaagtggaa cgaccagttc atcgtggacc caatccaagg cggtgcgggc | 300 |
| accagcatca acatgaacgc gaacgaggtg atcgcgaatc gtgcgctgga actgatgggc | 360 |
| gaggaaaagg gcaactacag caagattagc ccaaacagcc acgtgaatat gagccagagc | 420 |
| accaacgatg cgttcccaac ggccacccac atcgccgttc tgagtctgct gaatcagctc | 480 |
| atcgagacga ccaagtatat gcagcaagag ttcatgaaga aagcggatga gtttgcgggc | 540 |
| gtgatcaaga tgggtcgctg tcatctgcaa gatgcggtgc cgattctgct gggccaagag | 600 |
| ttcgaagcct acgcgcgcgt tatcgcgcgc gacattgaac gcatcgccaa caccccgcaac | 660 |
| aatctctacg acatcaacat gggcgcgacc gccgttggta cgggtctcaa cgccgaccca | 720 |
| gagtacatca gcatcgtgac cgaacatctg gccaaattca gtggtcaccc gctccgtagc | 780 |
| gcgcagcatc tcgtggatgc gacgcagaat accgattgct acacggaggt gagcagcgcg | 840 |
| ctcaaagtgt gcatgatcaa catgagcaaa atcgccaacg atctccgtct gatggccagt | 900 |
| ggtccacgtg ccggtctgag tgaaattgtt ctgccggcgc gtcaaccggg cagcagtatt | 960 |
| atcccgggtc tggttgcgcc agttatgccg gaggttatga atcaagttgc cttccaagtt | 1020 |
| ttcggtaacg atctgacgat cacgagcgcc agcgaagcgg gccagtttga gctcaacgtt | 1080 |
| atggagccgg ttctgttctt caacctcatc cagagcatta gcatcatgac gaatgtgttc | 1140 |
| aaaagcttta cggaaaactg cctcaaaggc atcaaggcca acgaggagcg tatgaaggag | 1200 |
| tacgtggaaa agagcatcgg catcatcacc gcgatcaatc cgcatgtggg ctatgaaacc | 1260 |
| gcggcgaagc tggcccgtga agcgtacctc accggtgaaa gcatccgcga gctgtgcatc | 1320 |
| aagtacggcg ttctcaccga ggagcagctg aacgagattc tgaacccgta tgagatgacg | 1380 |
| cacccgggta tcgccggtcg taagtaa | 1407 |

<210> SEQ ID NO 5
<211> LENGTH: 33
<212> TYPE: DNA
<213> ORGANISM: artificial sequence
<220> FEATURE:
<223> OTHER INFORMATION: F1primer

<400> SEQUENCE: 5

| | |
|---|---|
| gcgaagctgg cccgtcaggc gtacctcacc ggt | 33 |

<210> SEQ ID NO 6
<211> LENGTH: 21
<212> TYPE: DNA
<213> ORGANISM: artificial sequence
<220> FEATURE:
<223> OTHER INFORMATION: R1primer

<400> SEQUENCE: 6

| | |
|---|---|
| gccttactgg ttagcagaat g | 21 |